United States Patent
Cesarini et al.

(10) Patent No.: US 10,441,306 B2
(45) Date of Patent: Oct. 15, 2019

(54) RECIPROCATING ROTARY ARTHROSCOPIC SURGICAL INSTRUMENT

(71) Applicant: COVIDIEN LP, Mansfield, MA (US)

(72) Inventors: Peter M. Cesarini, Londonderry, NH (US); Karen Drucker, Danville, NH (US); Rafal Jezierski, Middleton, MA (US); Roger R. Cassidy, Methuen, MA (US)

(73) Assignee: COVIDIEN LP, Mansfield, MA (US)

( * ) Notice: Subject to any disclaimer, the term of this patent is extended or adjusted under 35 U.S.C. 154(b) by 253 days.

(21) Appl. No.: 15/584,377

(22) Filed: May 2, 2017

(65) Prior Publication Data

US 2017/0231654 A1 Aug. 17, 2017

Related U.S. Application Data

(63) Continuation of application No. 14/161,234, filed on Jan. 22, 2014, now Pat. No. 9,636,130, which is a
(Continued)

(51) Int. Cl.
*A61B 17/32* (2006.01)
*A61B 17/3207* (2006.01)
(Continued)

(52) U.S. Cl.
CPC ............. *A61B 17/32002* (2013.01); *A61B 17/320016* (2013.01); *A61B 17/320758* (2013.01);
(Continued)

(58) Field of Classification Search
CPC ...... A61B 17/32002; A61B 17/320758; A61B 17/320016; A61B 2017/320032;
(Continued)

(56) References Cited

U.S. PATENT DOCUMENTS 1,585,934 A 5/1926 Muir
1,666,332 A 4/1928 Hirsch
(Continued)

FOREIGN PATENT DOCUMENTS

DE 3339322 A1 5/1984
DE 3206381 C2 7/1986
(Continued)

OTHER PUBLICATIONS

Reexamination No. 95/001,933, Examiner's Answer dated Mar. 25, 2015 (3 pages).
(Continued)

*Primary Examiner* — Julian W Woo

(57) ABSTRACT

A surgical instrument includes a cutting member with an implement for cutting tissue, and a drive coupled to the cutting member to simultaneously rotate and translate the cutting member in response to a three applied to the drive. A method of cutting tissue includes positioning an outer member such that tissue is located within the outer member, engaging the tissue with an inner member, and simultaneously rotating and translating the inner member to cut the tissue. A tangential cutting force is applied to the tissue with the inner member to mechanically cut the tissue. The inner member is mechanically driven to undergo simultaneous rotation and translation.

19 Claims, 14 Drawing Sheets

Related U.S. Application Data continuation of application No. 13/051,257, filed on Mar. 18, 2011, now Pat. No. 8,663,264, which is a continuation of application No. 11/734,674, filed on Apr. 12, 2007, now Pat. No. 7,922,737, which is a continuation of application No. 09/983,810, filed on Oct. 26, 2001, now Pat. No. 7,226,459.

(51) Int. Cl.
  *A61B 18/14* (2006.01)
  *A61B 17/29* (2006.01)

(52) U.S. Cl.
  CPC ..... *A61B 18/148* (2013.01); *A61B 2017/2913* (2013.01); *A61B 2017/320028* (2013.01); *A61B 2017/320032* (2013.01); *A61B 2217/005* (2013.01)

(58) Field of Classification Search
  CPC .. A61B 2217/005; A61B 2017/320028; A61B 2017/2913; A61B 18/148
  See application file for complete search history.

(56) References Cited

U.S. PATENT DOCUMENTS

| | | |
|---|---|---|
| 1,831,786 A | 11/1931 | Duncan |
| 2,708,437 A | 5/1955 | Hutchins |
| 3,297,022 A | 1/1967 | Wallace |
| 3,686,706 A | 8/1972 | Finley |
| 3,734,099 A | 5/1973 | Bender et al. |
| 3,791,379 A | 2/1974 | Storz |
| 3,812,855 A | 5/1974 | Banko |
| 3,835,842 A | 9/1974 | Iglesias |
| 3,850,162 A | 11/1974 | Iglesias |
| 3,945,375 A | 3/1976 | Banko |
| 3,980,252 A | 9/1976 | Tae |
| 3,995,619 A | 12/1976 | Glatzer |
| 3,996,921 A | 12/1976 | Neuwirth |
| 4,011,869 A | 3/1977 | Seiler, Jr. |
| 4,108,182 A | 8/1978 | Hartman et al. |
| 4,146,405 A | 3/1979 | Timmer et al. |
| 4,198,958 A | 4/1980 | Utsugi |
| 4,203,444 A | 5/1980 | Bonnell et al. |
| 4,210,146 A | 7/1980 | Banko |
| 4,246,902 A | 1/1981 | Martinez |
| 4,247,180 A | 1/1981 | Norris |
| 4,258,721 A | 3/1981 | Parent et al. |
| 4,261,346 A | 4/1981 | Wettermann |
| 4,294,234 A | 10/1981 | Matsuo |
| 4,316,465 A | 2/1982 | Dotson, Jr. |
| 4,369,768 A | 1/1983 | Vukovic |
| 4,392,485 A | 7/1983 | Hiltebrandt |
| 4,414,962 A | 11/1983 | Carson |
| 4,449,538 A | 5/1984 | Corbitt et al. |
| 4,493,698 A | 1/1985 | Wang et al. |
| 4,517,977 A | 5/1985 | Frost |
| 4,543,965 A | 10/1985 | Pack et al. |
| 4,567,880 A | 2/1986 | Goodman |
| 4,589,414 A | 5/1986 | Yoshida et al. |
| 4,601,284 A | 7/1986 | Arakawa et al. |
| 4,601,290 A | 7/1986 | Effron et al. |
| 4,606,330 A | 8/1986 | Bonnet |
| 4,630,598 A | 12/1986 | Bonnet |
| 4,644,952 A | 2/1987 | Patipa et al. |
| 4,649,919 A | 3/1987 | Thimsen et al. |
| 4,700,694 A | 10/1987 | Shishido |
| 4,706,656 A | 11/1987 | Kuboto |
| 4,718,291 A | 1/1988 | Wood et al. |
| 4,737,142 A | 4/1988 | Heckele |
| 4,749,376 A | 6/1988 | Kensey et al. |
| 4,756,309 A | 7/1988 | Sachse et al. |
| 4,819,635 A | 4/1989 | Shapiro |
| 4,844,064 A | 7/1989 | Thimsen et al. |
| 4,850,354 A | 7/1989 | McGurk-Burleson et al. |
| 4,856,919 A | 8/1989 | Takeuchi et al. |
| 4,867,157 A | 9/1989 | McGurk-Burleson et al. |
| 4,924,851 A | 5/1990 | Ognier et al. |
| 4,940,061 A | 7/1990 | Terwilliger et al. |
| 4,950,278 A | 8/1990 | Sachse et al. |
| 4,955,882 A | 9/1990 | Hakky |
| 4,986,827 A | 1/1991 | Akkas et al. |
| 4,998,527 A | 3/1991 | Meyer |
| 4,998,914 A | 3/1991 | Wiest et al. |
| 5,007,917 A | 4/1991 | Evans |
| 5,027,792 A | 7/1991 | Meyer |
| 5,037,386 A | 8/1991 | Marcus et al. |
| 5,105,800 A | 4/1992 | Takahashi et al. |
| 5,106,364 A | 4/1992 | Hayafuji et al. |
| 5,112,299 A | 5/1992 | Pascaloff |
| 5,116,868 A | 5/1992 | Chen et al. |
| 5,125,910 A | 6/1992 | Freitas |
| 5,133,713 A | 7/1992 | Huang et al. |
| 5,152,744 A | 10/1992 | Krause et al. |
| 5,158,553 A | 10/1992 | Berry et al. |
| 5,163,433 A | 11/1992 | Kagawa et al. |
| 5,169,397 A | 12/1992 | Sakashita et al. |
| 5,176,677 A | 1/1993 | Wuchinich |
| 5,195,541 A | 3/1993 | Obenchain |
| 5,226,910 A | 7/1993 | Kajiyama et al. |
| 5,244,459 A | 9/1993 | Hill |
| 5,254,117 A | 10/1993 | Rigby et al. |
| 5,269,785 A | 12/1993 | Bonutti |
| 5,270,622 A | 12/1993 | Krause |
| 5,275,609 A | 1/1994 | Pingleton et al. |
| 5,288,290 A | 2/1994 | Brody |
| 5,304,118 A | 4/1994 | Trese et al. |
| 5,312,399 A | 5/1994 | Hakky et al. |
| 5,312,425 A | 5/1994 | Evans et al. |
| 5,312,430 A | 5/1994 | Rosenbluth et al. |
| 5,320,091 A | 6/1994 | Grossi et al. |
| 5,347,992 A | 9/1994 | Pearlman et al. |
| 5,350,390 A | 9/1994 | Sher |
| 5,364,395 A | 11/1994 | West, Jr. |
| 5,374,253 A | 12/1994 | Burns, Sr. et al. |
| 5,390,585 A | 2/1995 | Ryuh |
| 5,392,765 A | 2/1995 | Muller |
| 5,395,313 A | 3/1995 | Naves et al. |
| 5,403,276 A | 4/1995 | Schechter et al. |
| 5,409,013 A | 4/1995 | Clement |
| 5,409,453 A | 4/1995 | Lundquist et al. |
| 5,411,513 A | 5/1995 | Ireland et al. |
| 5,421,819 A | 6/1995 | Edwards et al. |
| 5,425,376 A | 6/1995 | Banys et al. |
| 5,429,601 A | 7/1995 | Conley et al. |
| 5,435,805 A | 7/1995 | Edwards et al. |
| 5,443,476 A | 8/1995 | Shapiro |
| 5,449,356 A | 9/1995 | Walbrink et al. |
| 5,456,673 A | 10/1995 | Ziegler et al. |
| 5,456,689 A | 10/1995 | Kresch et al. |
| 5,483,951 A | 1/1996 | Frassica et al. |
| 5,490,819 A | 2/1996 | Nicholas et al. |
| 5,490,860 A | 2/1996 | Middle |
| 5,492,537 A | 2/1996 | Vancaillie |
| 5,498,258 A | 3/1996 | Hakky et al. |
| 5,527,331 A | 6/1996 | Kresch et al. |
| 5,549,541 A | 8/1996 | Muller |
| 5,556,378 A | 9/1996 | Storz et al. |
| 5,563,481 A | 10/1996 | Krause |
| 5,569,164 A | 10/1996 | Lurz |
| 5,569,254 A | 10/1996 | Carlson et al. |
| 5,569,284 A | 10/1996 | Young et al. |
| 5,575,756 A | 11/1996 | Karasawa et al. |
| 5,591,187 A | 1/1997 | Dekel |
| 5,601,583 A | 2/1997 | Donahue et al. |
| 5,601,603 A | 2/1997 | Illi |
| 5,602,449 A | 2/1997 | Krause et al. |
| 5,603,332 A | 2/1997 | O'Connor |
| 5,630,798 A | 5/1997 | Beiser |
| 5,649,547 A | 7/1997 | Ritchart et al. |
| 5,669,927 A | 9/1997 | Boebel et al. |
| 5,672,945 A | 9/1997 | Krause |
| 5,674,179 A | 10/1997 | Bonnet et al. |
| 5,676,497 A | 10/1997 | Kim |

(56) References Cited

U.S. PATENT DOCUMENTS

| | | | |
|---|---|---|---|
| 5,695,448 A | 12/1997 | Kimura et al. |
| 5,702,420 A | 12/1997 | Sterling et al. |
| 5,709,698 A | 1/1998 | Adams et al. |
| 5,730,752 A | 3/1998 | Alden et al. |
| 5,733,298 A | 3/1998 | Berman |
| 5,741,286 A | 4/1998 | Recuset |
| 5,741,287 A | 4/1998 | Alden et al. |
| 5,749,885 A | 5/1998 | Sjostrom et al. |
| 5,749,889 A | 5/1998 | Bacich et al. |
| 5,759,185 A | 6/1998 | Grinberg |
| 5,772,634 A | 6/1998 | Atkinson |
| 5,775,333 A | 7/1998 | Burbank et al. |
| 5,782,849 A | 7/1998 | Miller |
| 5,807,240 A | 9/1998 | Muller et al. |
| 5,807,282 A | 9/1998 | Fowler |
| 5,810,770 A | 9/1998 | Chin et al. |
| 5,810,861 A | 9/1998 | Gaber |
| 5,814,009 A | 9/1998 | Wheatman |
| 5,833,643 A | 11/1998 | Ross et al. |
| 5,840,060 A | 11/1998 | Beiser et al. |
| 5,857,995 A | 1/1999 | Thomas et al. |
| 5,873,886 A | 2/1999 | Larsen et al. |
| 5,899,915 A | 5/1999 | Saadat |
| 5,911,699 A | 6/1999 | Anis et al. |
| 5,911,722 A | 6/1999 | Adler et al. |
| 5,913,867 A | 6/1999 | Dion |
| 5,916,229 A | 6/1999 | Evans |
| 5,925,055 A | 7/1999 | Adrian et al. |
| 5,928,163 A | 7/1999 | Roberts et al. |
| 5,944,668 A | 8/1999 | Vancaillie et al. |
| 5,947,990 A | 9/1999 | Smith |
| 5,951,490 A | 9/1999 | Fowler |
| 5,956,130 A | 9/1999 | Vancaillie et al. |
| 5,957,832 A | 9/1999 | Taylor et al. |
| 6,001,116 A | 12/1999 | Heisler et al. |
| 6,004,320 A | 12/1999 | Casscells et al. |
| 6,007,513 A | 12/1999 | Anis et al. |
| 6,024,751 A | 2/2000 | Lovato et al. |
| 6,032,673 A | 3/2000 | Savage et al. |
| 6,039,748 A | 3/2000 | Savage et al. |
| 6,042,552 A | 3/2000 | Cornier |
| 6,068,641 A | 5/2000 | Varsseveld |
| 6,086,542 A | 7/2000 | Glowa et al. |
| 6,090,094 A | 7/2000 | Clifford, Jr. et al. |
| 6,090,123 A | 7/2000 | Culp et al. |
| 6,113,594 A | 9/2000 | Savage |
| 6,119,973 A | 9/2000 | Galloway |
| 6,120,147 A | 9/2000 | Vijfvinkel et al. |
| 6,120,462 A | 9/2000 | Hibner |
| 6,132,448 A | 10/2000 | Perez et al. |
| 6,149,633 A | 11/2000 | Maaskamp |
| 6,156,049 A | 12/2000 | Lovato et al. |
| 6,159,160 A | 12/2000 | Hsei et al. |
| 6,159,209 A | 12/2000 | Hakky |
| 6,203,518 B1 | 3/2001 | Anis et al. |
| 6,217,543 B1 | 4/2001 | Anis et al. |
| 6,224,603 B1 | 5/2001 | Marino |
| 6,244,228 B1 | 6/2001 | Kuhn et al. |
| 6,258,111 B1 | 7/2001 | Ross et al. |
| 6,277,096 B1 | 8/2001 | Cortella et al. |
| 6,315,714 B1 | 11/2001 | Akiba |
| 6,358,200 B1 | 3/2002 | Grossi |
| 6,358,263 B2 | 3/2002 | Mark et al. |
| 6,359,200 B1 | 3/2002 | Day |
| 6,402,701 B1 | 6/2002 | Kaplan et al. |
| 6,428,486 B2 | 8/2002 | Ritchart et al. |
| 6,471,639 B2 | 10/2002 | Rudischhauser et al. |
| 6,494,892 B1 | 12/2002 | Ireland et al. |
| 6,585,708 B1 | 7/2003 | Maaskamp |
| 6,610,066 B2 | 8/2003 | Dinger et al. |
| 6,626,827 B1 | 9/2003 | Felix et al. |
| 6,632,182 B1 | 10/2003 | Treat |
| 6,656,132 B1 | 12/2003 | Ouchi |
| 6,712,773 B1 | 3/2004 | Viola |
| 6,824,544 B2 | 11/2004 | Boebel et al. |
| 6,837,847 B2 | 1/2005 | Ewers et al. |
| 7,025,720 B2 | 4/2006 | Boebel et al. |
| 7,025,732 B2 | 4/2006 | Thompson et al. |
| 7,150,713 B2 | 12/2006 | Shener et al. |
| 7,226,459 B2 | 6/2007 | Cesarini et al. |
| 7,249,602 B1 | 7/2007 | Emanuel |
| 7,510,563 B2 | 3/2009 | Cesarini et al. |
| 7,763,033 B2 | 7/2010 | Gruber et al. |
| 7,922,737 B1 | 4/2011 | Cesarini et al. |
| 8,061,359 B2 | 11/2011 | Emanuel |
| 8,062,214 B2 | 11/2011 | Shener et al. |
| 8,419,626 B2 | 4/2013 | Shener-Irmakoglu et al. |
| 8,663,264 B2 | 3/2014 | Cesarini et al. |
| 8,678,999 B2 | 3/2014 | Isaacson |
| 8,852,085 B2 | 10/2014 | Shener-Irmakoglu et al. |
| 8,893,722 B2 | 11/2014 | Emanuel |
| 8,932,208 B2 | 1/2015 | Kendale et al. |
| 8,951,274 B2 | 2/2015 | Adams et al. |
| 9,060,800 B1 | 6/2015 | Cesarini et al. |
| 9,060,801 B1 | 6/2015 | Cesarini et al. |
| 9,066,745 B2 | 6/2015 | Cesarini et al. |
| 9,072,431 B2 | 7/2015 | Adams et al. |
| 9,089,358 B2 | 7/2015 | Emanuel |
| 9,125,550 B2 | 9/2015 | Shener-Irmakoglu et al. |
| 9,155,454 B2 | 10/2015 | Sahney et al. |
| 9,636,130 B2 | 5/2017 | Cesarini et al. |
| 2001/0039963 A1 | 11/2001 | Spear et al. |
| 2001/0047183 A1 | 11/2001 | Privitera et al. |
| 2002/0058859 A1 | 5/2002 | Brommersma |
| 2002/0165427 A1 | 11/2002 | Yachia et al. |
| 2003/0050603 A1 | 3/2003 | Todd |
| 2003/0050638 A1 | 3/2003 | Yachia et al. |
| 2003/0078609 A1 | 4/2003 | Finlay et al. |
| 2003/0114875 A1 | 6/2003 | Sjostrom |
| 2004/0204671 A1 | 10/2004 | Stubbs et al. |
| 2005/0043690 A1 | 2/2005 | Todd |
| 2005/0085692 A1 | 4/2005 | Kiehn et al. |
| 2006/0036132 A1 | 2/2006 | Renner et al. |
| 2006/0047185 A1 | 3/2006 | Shener et al. |
| 2006/0241586 A1 | 10/2006 | Wilk |
| 2008/0001562 A1 | 1/2008 | Hobbet et al. |
| 2008/0015621 A1 | 1/2008 | Emanuel |
| 2008/0058588 A1 | 3/2008 | Emanuel |
| 2008/0058842 A1 | 3/2008 | Emanuel |
| 2008/0097468 A1 | 4/2008 | Adams et al. |
| 2008/0097469 A1 | 4/2008 | Gruber et al. |
| 2008/0097470 A1 | 4/2008 | Gruber et al. |
| 2008/0097471 A1 | 4/2008 | Adams et al. |
| 2008/0135053 A1 | 6/2008 | Gruber |
| 2008/0146872 A1 | 6/2008 | Gruber et al. |
| 2008/0146873 A1 | 6/2008 | Adams et al. |
| 2008/0245371 A1 | 10/2008 | Gruber |
| 2008/0249366 A1 | 10/2008 | Gruber et al. |
| 2008/0249534 A1 | 10/2008 | Gruber et al. |
| 2008/0249553 A1 | 10/2008 | Gruber et al. |
| 2008/0262308 A1 | 10/2008 | Prestezog et al. |
| 2009/0082628 A1 | 3/2009 | Kucklick et al. |
| 2009/0270812 A1 | 10/2009 | Litscher et al. |
| 2009/0270895 A1 | 10/2009 | Churchill et al. |
| 2009/0270896 A1 | 10/2009 | Sullivan et al. |
| 2009/0270897 A1 | 10/2009 | Adams et al. |
| 2009/0270898 A1 | 10/2009 | Chin et al. |
| 2010/0087798 A1 | 4/2010 | Adams et al. |
| 2010/0152647 A1 | 6/2010 | Shener et al. |
| 2011/0166419 A1 | 7/2011 | Reif et al. |
| 2012/0078038 A1 | 3/2012 | Sahney et al. |
| 2013/0131452 A1 | 5/2013 | Kuroda et al. |
| 2014/0031834 A1 | 1/2014 | Germain et al. |

FOREIGN PATENT DOCUMENTS

| | | |
|---|---|---|
| DE | 3601453 A1 | 9/1986 |
| DE | 3615694 A1 | 11/1987 |
| DE | 4038398 A1 | 6/1992 |
| DE | 440035 A1 | 5/1996 |
| DE | 19633124 A1 | 5/1997 |
| DE | 19751632 C1 | 9/1999 |
| DE | 102006022827 A1 | 12/2006 |
| EP | 0310285 A2 | 4/1989 |

(56) References Cited

FOREIGN PATENT DOCUMENTS

| | | |
|---|---|---|
| EP | 0327410 A1 | 8/1989 |
| EP | 0557044 A1 | 8/1993 |
| EP | 0582295 A2 | 2/1994 |
| EP | 0606531 A2 | 7/1994 |
| EP | 0621008 A2 | 10/1994 |
| EP | 0806183 A1 | 11/1997 |
| EP | 1681022 A1 | 7/2006 |
| GB | 2093353 A | 9/1982 |
| GB | 2311468 A | 10/1997 |
| JP | 2002529185 A | 9/2002 |
| JP | 2002 538889 A | 11/2002 |
| JP | 2003245247 A | 9/2003 |
| WO | 8101648 A1 | 6/1981 |
| WO | 9211816 A2 | 7/1992 |
| WO | 9307821 A1 | 4/1993 |
| WO | 9315664 A1 | 8/1993 |
| WO | 9426181 A1 | 11/1994 |
| WO | 9505777 A1 | 3/1995 |
| WO | 9510981 A1 | 4/1995 |
| WO | 9510982 A1 | 4/1995 |
| WO | 9522935 A1 | 8/1995 |
| WO | 9530377 A1 | 11/1995 |
| WO | 9611638 A1 | 4/1996 |
| WO | 9626676 A1 | 9/1996 |
| WO | 9709922 A1 | 3/1997 |
| WO | 9717027 A1 | 5/1997 |
| WO | 9719642 A1 | 6/1997 |
| WO | 9724071 A1 | 7/1997 |
| WO | 9734534 A1 | 9/1997 |
| WO | 9735522 A1 | 10/1997 |
| WO | 9809569 A1 | 3/1998 |
| WO | 9810707 A1 | 3/1998 |
| WO | 9846147 A1 | 10/1998 |
| WO | 9903407 A1 | 1/1999 |
| WO | 9903409 A1 | 1/1999 |
| WO | 9907295 A1 | 2/1999 |
| WO | 1006944 C2 | 3/1999 |
| WO | 9911184 A1 | 3/1999 |
| WO | 9939648 A1 | 8/1999 |
| WO | 9944506 A1 | 9/1999 |
| WO | 9960935 A1 | 12/1999 |
| WO | 0012010 A1 | 3/2000 |
| WO | 2000/28890 A1 | 5/2000 |
| WO | 0033743 A1 | 6/2000 |
| WO | 0044295 A1 | 8/2000 |
| WO | 0047116 A1 | 8/2000 |
| WO | 0057797 A1 | 10/2000 |
| WO | 2001/35831 A1 | 5/2001 |
| WO | 2001/58368 A1 | 8/2001 |
| WO | 200195810 A2 | 12/2001 |
| WO | 02069808 A2 | 9/2002 |
| WO | 03022164 A1 | 3/2003 |
| WO | 03077767 A1 | 9/2003 |
| WO | 2005060842 A1 | 7/2005 |
| WO | 2005096963 A2 | 10/2005 |
| WO | 2006105283 A2 | 10/2006 |
| WO | 2006121968 A2 | 11/2006 |
| WO | 2006121970 A2 | 11/2006 |
| WO | 2007044833 A2 | 4/2007 |
| WO | 2012044705 A1 | 4/2012 |

OTHER PUBLICATIONS

Reexamination No. 95/001,933, Executed Expert Declaration of Hal Walbrink in support of Request for Inter Partes Reexamination of U.S. Pat. No. 7,226,459, Executed Mar. 9, 2012 (42 pages).
Reexamination No. 95/001,933, First Office Action dated Jun. 5, 2012 (37 pages).
Reexamination No. 95/001,933, Litigation Search Report CRU 3999 dated Mar. 29, 2012 (24 pages).
Reexamination No. 95/001,933, Order Granting Request for Reexamination dated Jun. 5, 2012 (29 pages).
Reexamination No. 95/001,933, Patent Owner's Apr. 14, 2014 Appeal Brief (334 pages).
Reexamination No. 95/001,933, Patent Owner's dated Feb. 13, 2014 Notice of Appeal (2 pages).
Reexamination No. 95/001,933, Patent Owner's Aug. 6, 2012 Response to First Office Action dated Jun. 5, 2012 (156 pages).
Reexamination No. 95/001,933, Patent Owner's Jun. 3, 2013 Response to Second Office Action mdated Apr. 1, 2013 (37 pages).
Reexamination No. 95/001,933, Patent Owner's Oct. 21, 2013 Response to Action Closing Prosecution dated Sep. 19, 2013 (180 pages).
Reexamination No. 95/001,933, Right of Appeal Notice dated Jan. 14, 2014 (58 pages).
Reexamination No. 95/001,933, Second Office Action dated Apr. 1, 2013 (56 pages).
Reexamination No. First 95/001,933, Third Party's Dec. 19, 2012 Response to Notification of Defective Paper and Comments on Office Action dated Jun. 5, 2012 (38 pages).
Reexamination No. 95/001,933, Third Party's Jul. 3, 2013 Comments on Second Office Action dated Apr. 1, 2013 (62 pages).
Reexamination No. 95/001,933, Third Party's Mar. 12, 2012 Request for Inter Partes Reexamination of U.S. Pat. No. 7,226,459 (130 pages).
Reexamination No. 95/001,933, Third Party's May 14, 2014 Respondent's Brief (303 pages).
Reexamination No. 95/001,933, Third Party's Nov. 20, 2013 Comments on Action Closing Prosecution dated Sep. 19, 2013 (38 pages).
Reexamination No. 95/001,933, Third Party's Sep. 5, 2012 Comments on First Office Action dated Jun. 5, 2012 (210 pages).
Reexamination No. 95/001,955, Appendix 19 to Request for Inter Partes Reexamination of U.S. Pat. No. 8,061,359, Opening Claim Construction Brief of Defendant Hologic, Inc., dated Feb. 24, 2012, in *Smith & Nephew, Inc.* v. *Hologic, Inc.*, Civil ActionNo. 11-12064-RWZ, U.S. District Court for the District of Massachusetts (24 pages).
Reexamination No. 95/001,955, Appendix 20 to Request for Inter Partes Reexamination of U.S. Pat. No. 8,061,359, Opening Markman Brief of Plaintiff Smith & Nephew, Inc., dated Feb. 24, 2012, in *Smith & Nephew, Inc.* v. *Hologic, Inc.*, Civil Action No. 11-12064-RWZ, U.S. District Court for the District of Massachusetts (24 pages).
Reexamination No. 95/001,955, Appendix 28 to Request for Inter Partes Reexamination of U.S. Pat. No. 8,061,359, Claim chart for anticipation of claims 1-8 based on U.S. Pat. No. 5,456,689 to Kresch (4 pages).
Reexamination No. 95/001,955, Appendix 29 to Request for Inter Partes Reexamination of U.S. Pat. No. 8,061,359, Claim chart for anticipation of claims 1-8 based on U.S. Pat. No. 6,032,673 to Savage (13 pages).
Reexamination No. 95/001,955, Appendix 30 to Request for Inter Partes Reexamination of U.S. Pat. No. 8,061,359, Claim chart for anticipation of claims 1-8 based on U.S. Pat. No. 3,945,375 to Banko (4 pages).
Reexamination No. 95/001,955, Decision Denying Petition dated Sep. 28, 2012 (5 pages).
Reexamination No. 95/001,955, Executed Expert Declaration of Dr. Henry A. Dominicis in support of Request for Inter Partes Reexamination of U.S. Pat. No. 8,061,359, Executed Apr. 1, 2012 (150 pages).
Reexamination No. 95/001,955, Executed Expert Declaration of Hal Walbrink in support of Request for Inter Partes Reexamination of U.S. Pat. No. 8,061,359, Executed Apr. 2, 2012 (22 pages).
Reexamination No. 95/001,955, Litigation Search Report CRU 3999 dated Apr. 3, 2012 (33 pages).
Reexamination No. 95/001,955, Order Denying Request for Inter Partes Reexamination dated Jun. 4, 2012 (35 pages).
Reexamination No. 95/001,955, Request for Inter Partes Reexamination of U.S. Pat. No. 8,061,359, filed Apr. 2, 2012 (265 pages).
Reexamination No. 95/001,955, Request for Reconsideration of Third Party Requestor's Petition for Reexamination dated Jul. 3, 2012 (32 pages).

(56) References Cited

OTHER PUBLICATIONS

Reexamination No. 95/002,058, Executed Expert Declaration of Dr. Henry A. Dominicis in support of Request for Inter Partes Reexamination of U.S. Pat. No. 8,061,359, Executed Jul. 24, 2012 (101 pages).
Reexamination No. 95/002,058, First Action Closing Prosecution dated Aug. 9, 2013 (34 pages).
Reexamination No. 95/002,058, First Office Action dated Sep. 19, 2012 (37 pages).
Reexamination No. 95/002,058, Litigation Search Report CRU 3999 dated Aug. 13, 2012 (29 pages).
Reexamination No. 95/002,058, Patent Owner's Mar. 5, 2015 Notice of Appeal (2 pages).
Reexamination No. 95/002,058, Patent Owner's Jan. 22, 2013 Response to First Office Action dated Sep. 19, 2012 (379 pages).
Reexamination No. 95/002,058, Patent Owner's Mar. 24, 2014 Response to Second Office Action dated Jan. 24, 2014 (55 pages).
Reexamination No. 95/002,058, Patent Owner's Sep. 29, 2014 Response to Second Action Closing Prosecution dated Aug. 27, 2014 (12 pages).
Reexamination No. 95/002,058, Patent Owner's Sep. 9, 2013 Response to First Action Closing Prosecution dated Aug. 9, 2013 (159 pages).
Reexamination No. 95/002,058, Reexam Order dated Sep. 19, 2012 (54 pages).
Reexamination No. 95/002,058, Right of Appeal Notice dated Feb. 4, 2015 (35 pages).
Reexamination No. 95/002,058, Second Action Closing Prosecution dated Aug. 27, 2014 (35 pages).
Reexamination No. 95/002,058, Second Office Action dated Jan. 24, 2014 (31 pages).
Reexamination No. 95/002,058, Third Party's Apr. 23, 2014 Comments on Second Office Action dated Jan. 24, 2014 (117 pages).
Reexamination No. 95/002,058, Third Party's Feb. 21, 2013 Comments on First Office Action dated Sep. 19, 2012 (771 pages).
Reexamination No. 95/002,058, Third Party's Jul. 24, 2012 Request for Inter Partes Reexamination of U.S. Pat. No. 8,061,359 (1050 pages).
Reexamination No. 95/002,058, Third Party's Oct. 19, 2012 Request for Reconsideration of Certain Decisions Regarding Third Party Requestor's Request for Reexamination of U.S. Pat. No. 8,061,359 (19 pages).
Reexamination No. 95/002,058, Third Party's Oct. 29, 2014 Comments on Second Action Closing Prosecution dated Aug. 27, 2014 (31 pages).
Reexamination No. 95/002,058, Third Party's Oct. 9, 2013 Comments on First Action Closing Prosecution dated Aug. 9, 2013 (25 pages).
Reference AQ "Fishing Reel produced and sold by Shimano of Japan in to the U.S. prior to Oct. 26, 2001," as cited in the IDS filed Oct. 17, 2005 in the prosecution file history of U.S. Appl. No. 09/983,810 (7 pages).
Reexamination No. 95/001,933, Patent Trial and Appeal Board's Jan. 20, 2016 Decision on Appeal (35 pages).
Reexamination No. 95/002,058, Patent Owner's May 5, 2015 Appeal Brief (47; pages).
Reexamination No. 95/002,058, Third Party's Jun. 5, 2015 Respondent Brief (21; pages).
Reexamination No. 95/002,058, Third Party's Jul. 24, 2015 Resubmitted; Respondent Brief (21 pages).
Reexamination No. 95/002,058, Examiner's Answer dated Sep. 17, 2015 (3; pages).
Reexamination No. 95/002,058, Patent Owner's Oct. 19, 2015 Rebuttal Brief; (25 pages).
ACMI Corporation, "Dolphin II Hysteroscopic Fluid Management Systems," ACMI Corporation, 2002 (1 page).
ACMI Corporation, "Dolphin II and DISTEN-U-FLO Fluid Management Systems for Hysteroscopy", ACMI Corporation, 2002 (1 page).

Bacsko "Uterine Surgery by Operative Hysteroscopy", European Journal of Obstetrics & Gynecology and Reproductive Biology, vol. 71, pp. 219-222, 1997 (4 pages).
Baggish et al., "Diagnostic and Operative Hysterectomy," Mosby, pp. 97-105, 123-125, 127-132, 353-355, and 394-398, 1999 (27 pages).
C.R. Bard, Inc, "The HydroFlex HD System" (1 page).
Cravello et al., "Hysteroscopic Resection of Fibroids: Results with a 6-Year Follow-up Period", Journal of Gynecologic Surgery, vol. 15, No. 1, 1-5 1999 (5 pages).
Defendant Hologic Inc.'s Preliminary, Non-Binding List of Asserted Prior Art References, dated Feb. 8, 2012, in *Smith & Nephew, Inc. v. Hologic, Inc.*, Civil Action Nos. 11-12064-RWZ and 10-10951-RWZ, U.S. District Court for the District of Massachusetts (7 pages).
Dictionary definition of translate, Merriam-Webster Dictionary, on-line edition, retrieved Mar. 20, 2013 (1 page).
Drews et al., "Surgical Approach to Myomas: Laparoscopy and Hysteroscopy", Seminars in Reproductive Endocrinology, vol. 10, No. 4, pp. 367-377, 1992 (11 pages).
Dumesic et al., "A New Approach to Hysteroscopic Cannulation of the Fallopian Tube", Journal of Gynecologic Surgery, vol. 7, No. 1, pp. 7-9, 1991 (3 pages).
Emanuel et al., "Long-term Results of Hysteroscopic Myomectomy for Abnormal Uterine Bleeding", Obstetrics & Gynecoogy, vol. 93, No. 5, Part I, pp. 743-748, 1999 (6 pages).
European Patent Application No. 05 786 521.4-2305, Examination Report dated Apr. 21, 2010 (4 pages).
European Patent Application No. 05 786 521.4-2305, Examination Report dated Sep. 26, 2012 (5 pages).
European Patent Application No. 11 770 261.3-1657, Examination Report dated Feb. 11, 2014 (4 pages).
Franchini et al., "Endometrial resection: a diagnostic tool in postmenopausal women", Gynecological Endoscopy, 8, pp. 111-114, 1999 (5 pages).
"From Distention to Deficit Monitoring Taking the All-In-One Approach", W.O.M. World of Medicine (1 page).
Gerber et al., "The Endoscapel: A new endoscopic instrument for supracervical hysterectomy and morcellation of masses; clinical evaluation", European Journal of Obstetrics & Gynecology and Reproductive Biology, 86, p. S12, 1999 (1 page).
Gynecare "Motor Drive Unit" Instructions for Use (3 pages).
Gynecare X-Tract, "Tissue Morcellator", Instructions for Use (3 pages).
Gynecare, "Fluid Management System" Instructions for Use (26 pages).
Gynescope Corporation "Laser Fiber Director", Advertisement, Journal of Gynecologic Surgery, vol. 6, No. 1, 1990 (2 pages).
Hess et al., "Textbook of Bilio-Pancreatic Disease", vol. III, PICCIN, e.g. Fig 6.5.1, pp. 1584-1586, 1997 (5 pages).
Hologic's Opposition to Smith & Nephew's Motion for Preliminary Injunction, Redacted, filed Dec. 30, 2011, in *Smith & Nephew, Inc. v. Hologic, Inc.*, Civil Action No. 11-12064-RWZ, U.S. District Court for the District of Massachusetts (26 pages).
"HysteRo-Purator 1143-1 Technical Data" WISAP (2 pages).
International Application No. PCT/US2005/029807, International Preliminary Report on Patentability dated Feb. 28, 2007 (9 pages).
International Application No. PCT/US2005/029807, International Search Report dated Jun. 13, 2006 (5 pages).
International Application No. PCT/US2011/053753, International Preliminary Report on Patentability dated Apr. 2, 2013 (7 pages).
International Application No. PCT/US2011/053753, International Search Report dated Dec. 20, 2011 (4 pages).
Japanese Patent Application No. 2007-530014, Translation of Office Action dated Feb. 15, 2011 (10 pages).
Karl Storz "Pilot a Course to Successful Outcomes", Intermetro Industries Corporation, 2001 (2 pages).
Karl Storz "Uterine Resectoscopes for Endometrial Ablation and Resection", Advertisement, Journal of Gynecologic Surgery, vol. 6, No. 1, 1990 (3 pages).
Karl Storz, Advertisement, Journal of Gynecologic Surgery, vol. 5, No. 4, 1989 (3 pages).

(56) References Cited

OTHER PUBLICATIONS

Lin et al. "Clinical Applications of a New Fujinon Operating Fiberoptic Hysteroscope", Journal of Gynecologic Surgery, vol. 6, No. 2, pp. 81-87, 1990 (7 pages).
Mettler et al., "Pelviscopic uterine surgery" Surgical Endoscopy, 6, pp. 23-31, 1992 (9 pages).
Niels et al., "Hysteroscopy: Textbook and Atlas", Thieme Medical Publishers, pp. 91-103, 1994 (13 pages).
Nisolle et al., "Endometrial ablation with the Nd-YAG laser in dysfunctional bleeding" Minimally Invasive Therapy, vol. 1, pp. 35-39, 1991 (5 pages).
Olympus Product Catalogue: Part No. A2461—OP Nephroscope, Sep. 1991 (3 pages).
Park et al., "Endoscopic Management of Uterine Myoma", Yonsei Medical Journal, vol. 40, No. 6, pp. 583-588, 1999 (6 pages).
Reexamination No. 95/001,933, Action Closing Prosecution dated Sep. 19, 2013 (41 pages).
Reexamination No. 95/001,933, Appendices 14-28 to Request for Inter Partes Reexamination of U.S. Pat. No. 7,226,459, Claim Charts for Various Claims in view of Various References (436 pages).
Reexamination No. 95/001,933, Appendix 2 to Request for Inter Partes Reexamination of U.S. Pat. No. 7,226,459, Memorandum of Decision dated Apr. 21, 2011, in *Smith & Nephew, Inc.* v. *Interlace Medical, Inc.*, Civil Action No. 10-10951-RWZ, U.S.District Court for the District of Massachusetts (14 pages).
Reexamination No. 95/001,933, Appendix 6 to Request for Inter Partes Reexamination of U.S. Pat. No. 7,226,459, Opening Markman Brief of Plaintiff Smith & Nephew, Inc. dated Oct. 13, 2010, in *Smith & Nephew, Inc.* v. *Interlace Medical, Inc.*, CivilAction No. 10-10951-RWZ, U.S. District Court for the District of Massachusetts (23 pages).
Reexamination No. 95/001,933, Appendix 7 to Request for Inter Partes Reexamination of U.S. Pat. No. 7,226,459, Defendant Interlace Medical, Inc's Responsive Markman Brief (Redacted) dated Oct. 27, 2010, in *Smith & Nephew, Inc.* v. *Interlace Medical, Inc.*, Civil Action No. 10-10951-RWZ, U.S. District Court for the District of Massachusetts (26 pages).
Reexamination No. 95/001,933, Appendix 8 to Request for Inter Partes Reexamination of U.S. Pat. No. 7,226,459, Plaintiff Smith & Nephew, Inc.'s Reply in Support of Markman Brief dated Nov. 3, 2010, in *Smith & Nephew, Inc.* v. *Interlace Medical, Inc.*,Civil Action No. 10-10951-RWZ, U.S. District Court for the District of Massachusetts (8 pages).
Richard Wolf "'Morce—Power 2306' Electronic Morcellator" (2 pages).
Richard Wolf "The Fluid Manager" (2 pages).
Sheth, "Fiberoptic Light for Oophorectomy at Vaginal Hysterectomy", Journal of Gynecologic Surgery, vol. 14, No. pp. 119-122, 1998 (4 pages).
Sugimoto "A Color Atlas of Hysteroscopy" Springer-Verlag Tokyo, 1999 (17 pages).
U.S. Appl. No. 09/486,977, Office Action dated Sep. 7, 2005 (7 pages).
U.S. Appl. No. 11/780,759, Applicant's Mar. 31, 2011 Response to Office Action dated Jan. 5, 2010 (15 pages).
U.S. Appl. No. 11/780,759, Applicant's Oct. 25, 2010 Response to Office Action dated Jul. 26, 2010 (13 pages).
U.S. Appl. No. 11/780,759, Office Action dated Jan. 5, 2011 (7 pages).
U.S. Appl. No. 11/780,759, Office Action dated Jul. 22, 2010 (5 pages).
U.S. Appl. No. 11/780,759, Office Action dated Jul. 26, 2010 (7 pages).
U.S. Appl. No. 11/929,938, Office Action dated Jan. 5, 2011 (10 pages).
U.S. Appl. No. 11/929,938, Office Action dated Jul. 30, 2010 (10 pages).
U.S. Appl. No. 11/929,940, Advisory Action dated Sep. 10, 2010 (3 pages).
U.S. Appl. No. 11/929,940, Office Action dated Dec. 30, 2009 (9 pages).
U.S. Appl. No. 11/929,940, Office Action dtaed Jul. 1, 2010 (12 pages).
Valle "Hysteroscopic Removal of Submucous Leiomyomas", Journal of Gynecologic Surgery, vol. 6, No. 1, pp. 89-96, 1990 (9 pages).
Weck "A Direct Path to Diagnostic and Operative Control: The Weck-Baggish Hysteroscopy System" Advertisement, Journal of Gynecologic Surgery, vol. 7, No. 1, 1991 (2 pages).
Williamson et al., Editorial 1 "Complications of hysteroscopic treatments of menorrhagia", British Journal of Anesthesia, vol. 77, No. 3, pp. 305-308, 1996 (4 pages).
Reexamination No. 95/002,058, Patent Owner's Jul. 1, 2015 Corrected Appeal Brief (47 pages).
Reexamination No. 95/001,933, Patent Owner's Apr. 24, 2015 Rebuttal Brief (8 pages).
Examination Report issued in European Application No. 11004648.9 dated Feb. 21, 2019, 4 pages.

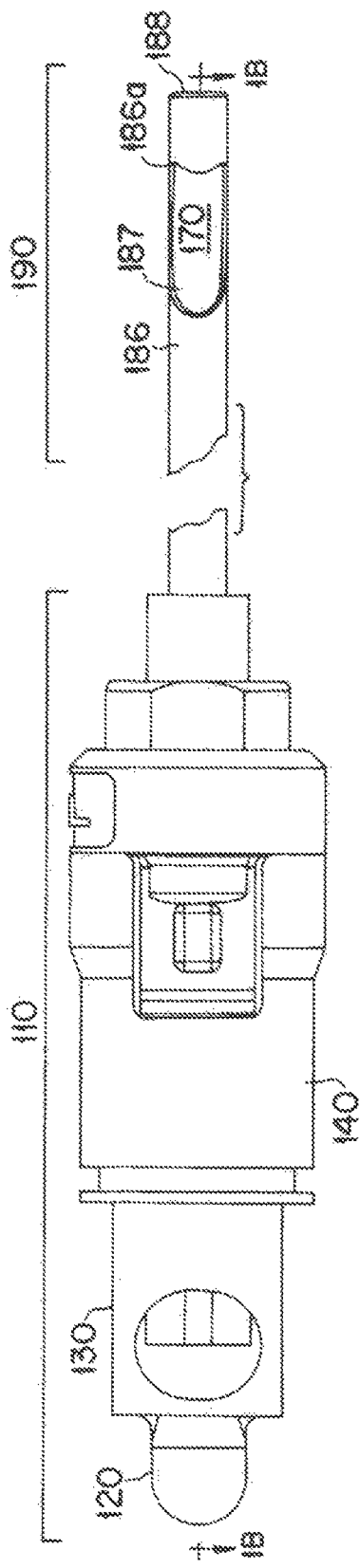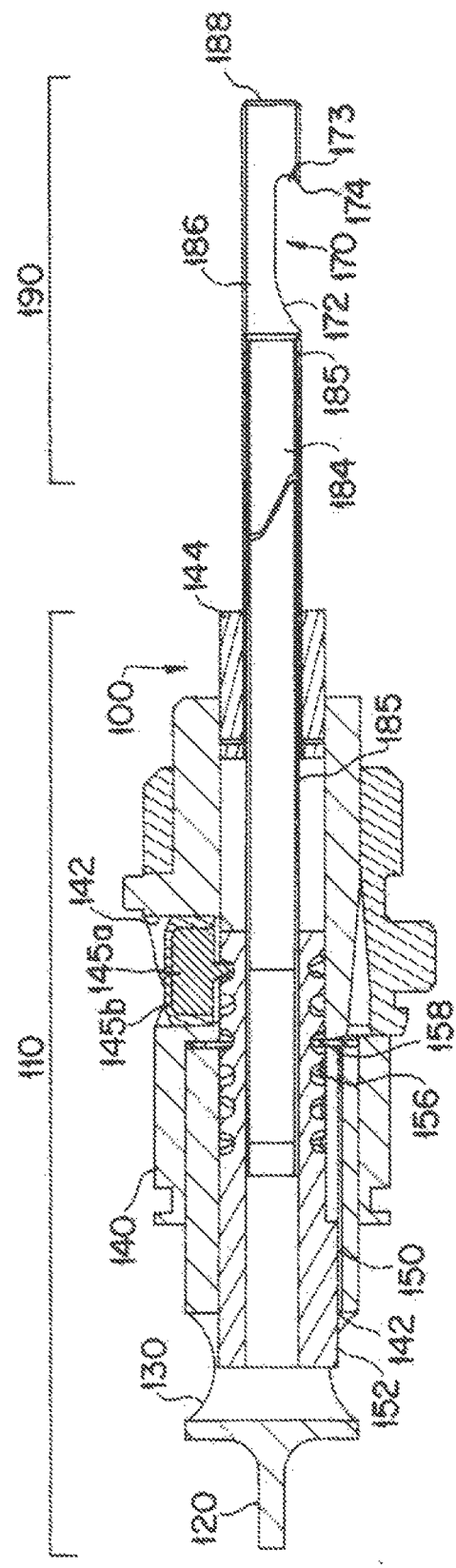

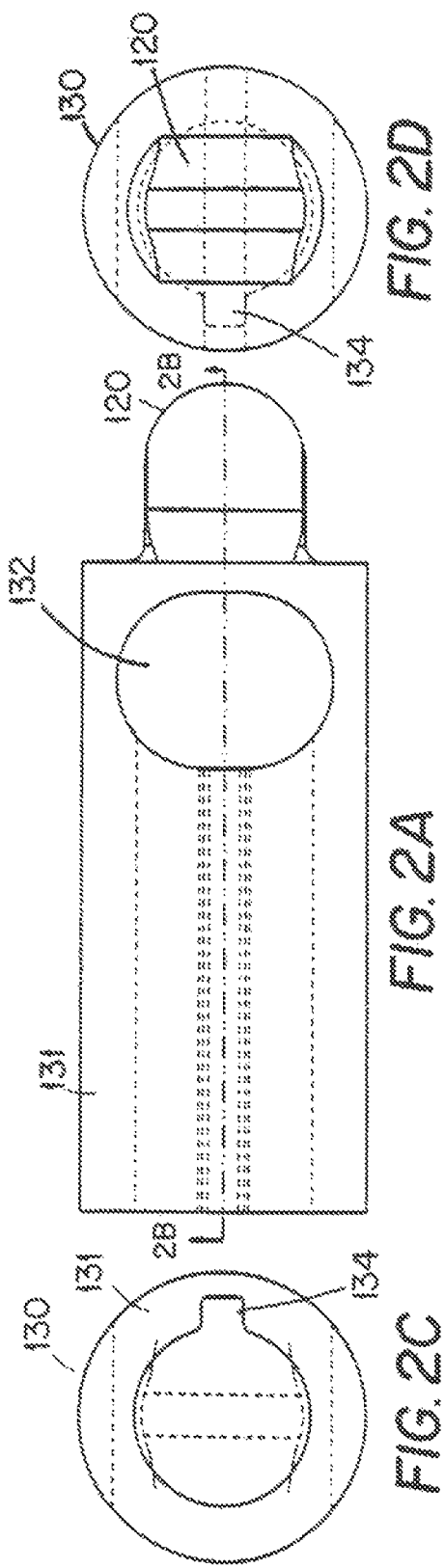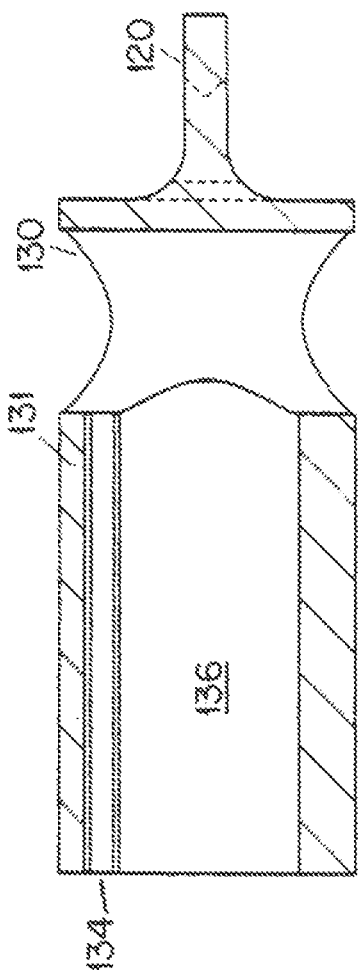

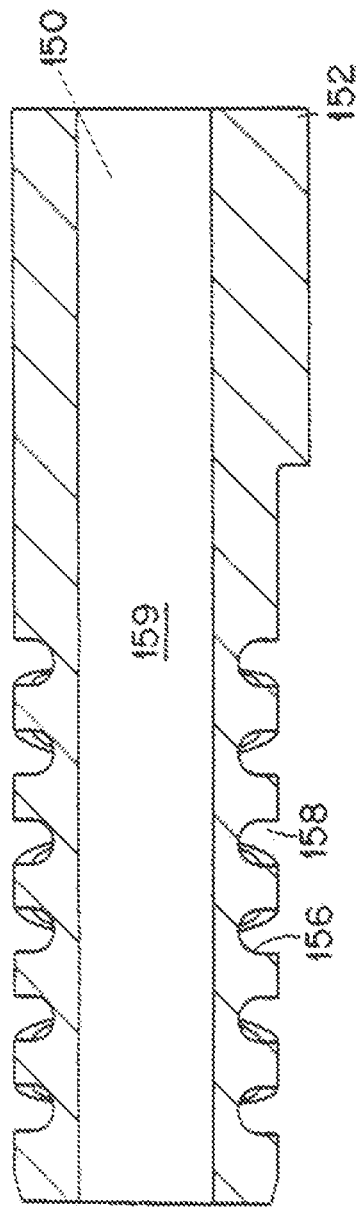
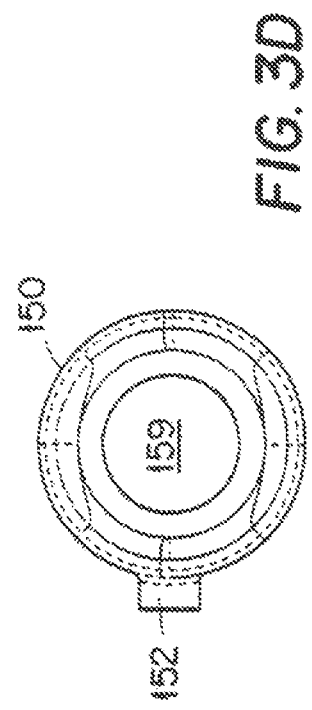

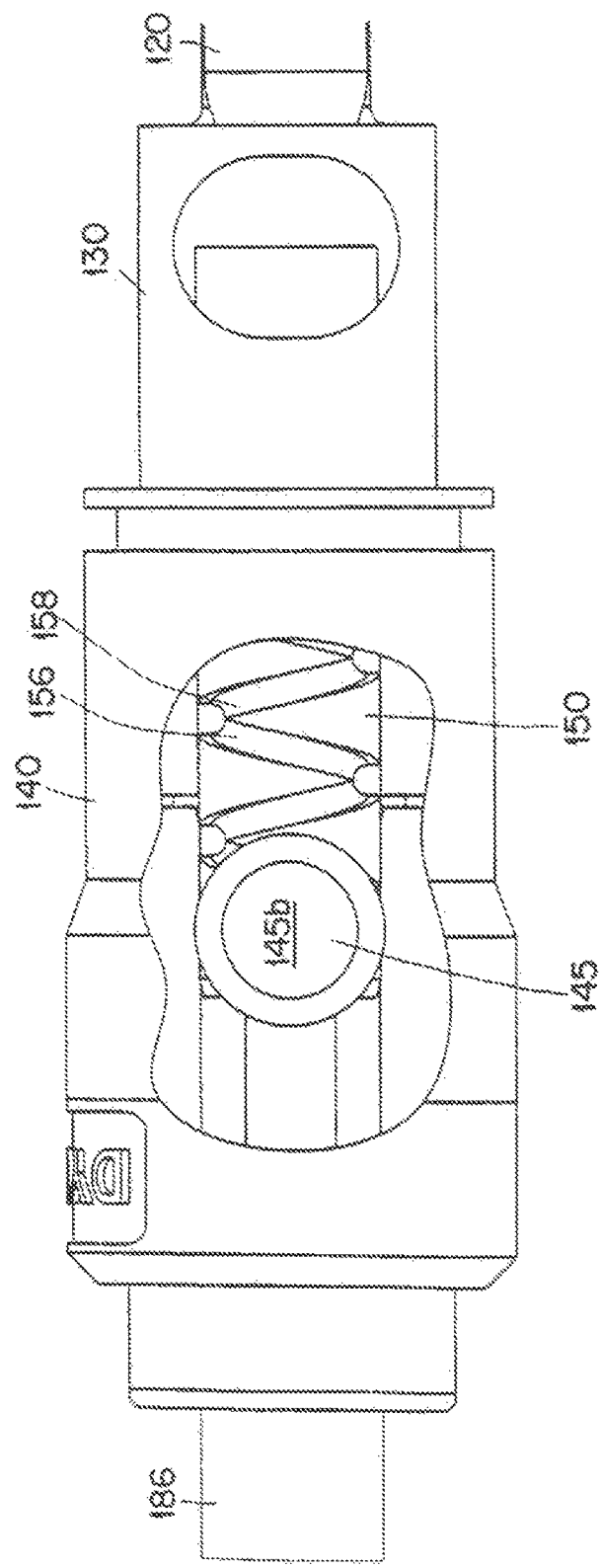

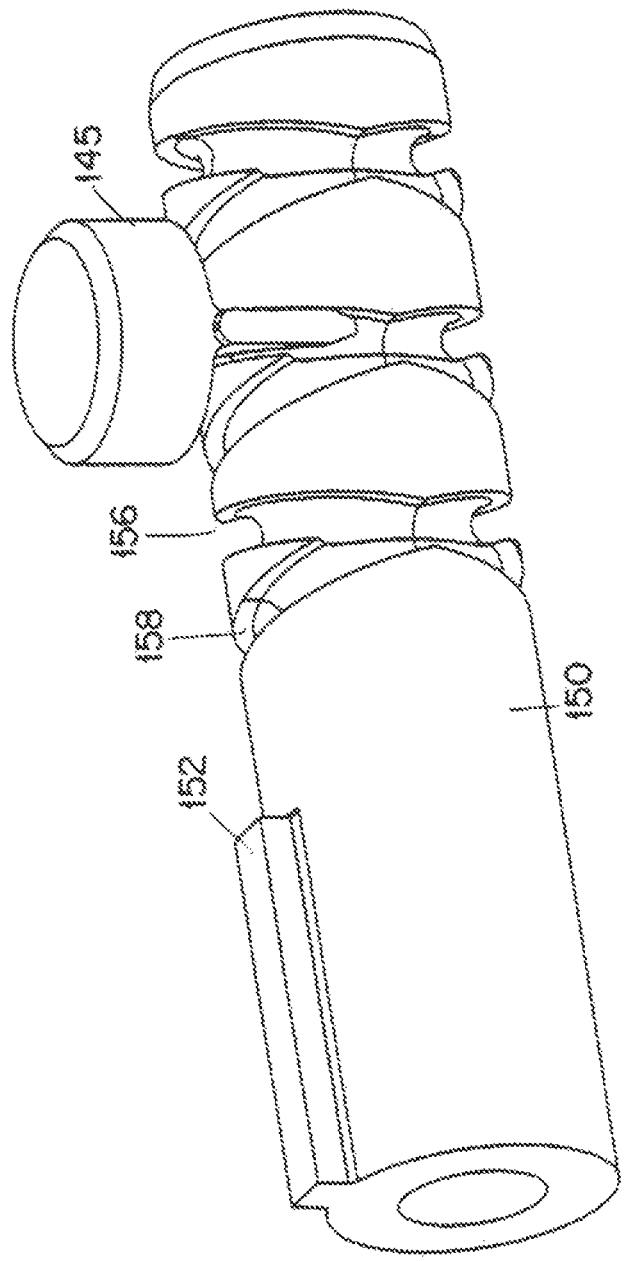

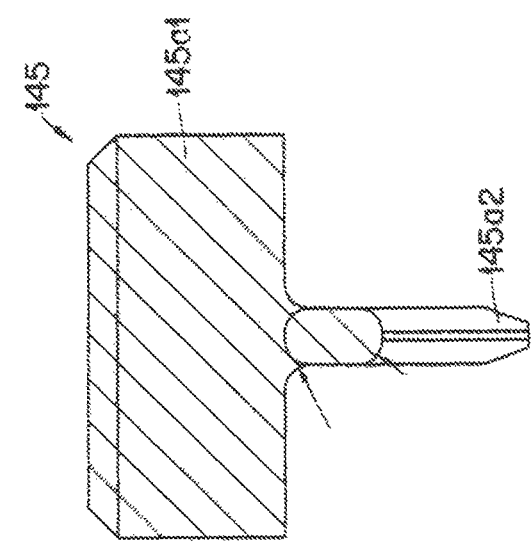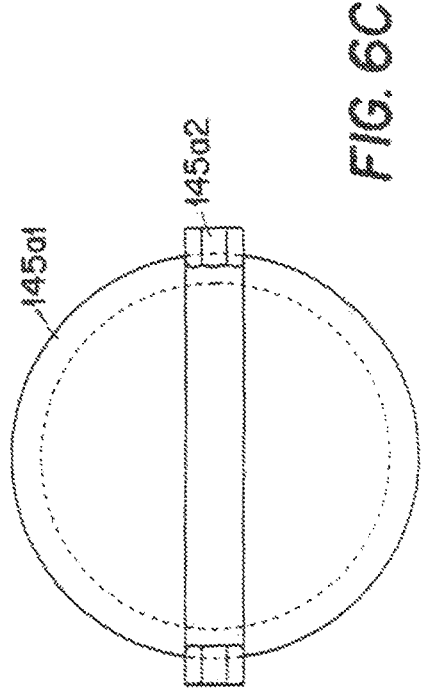

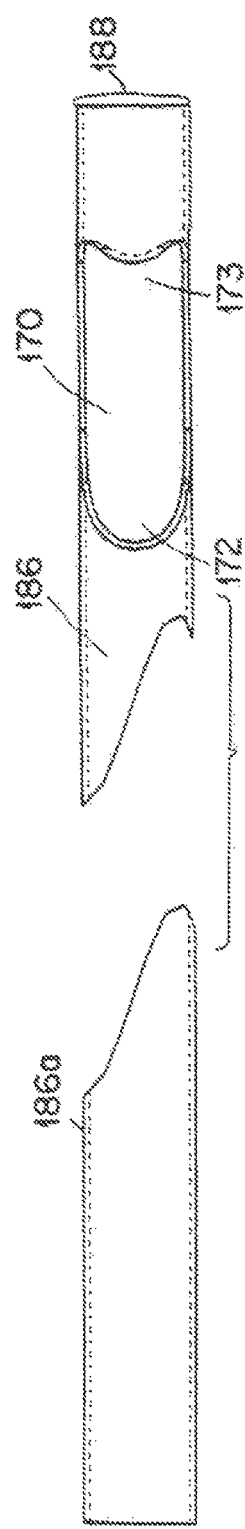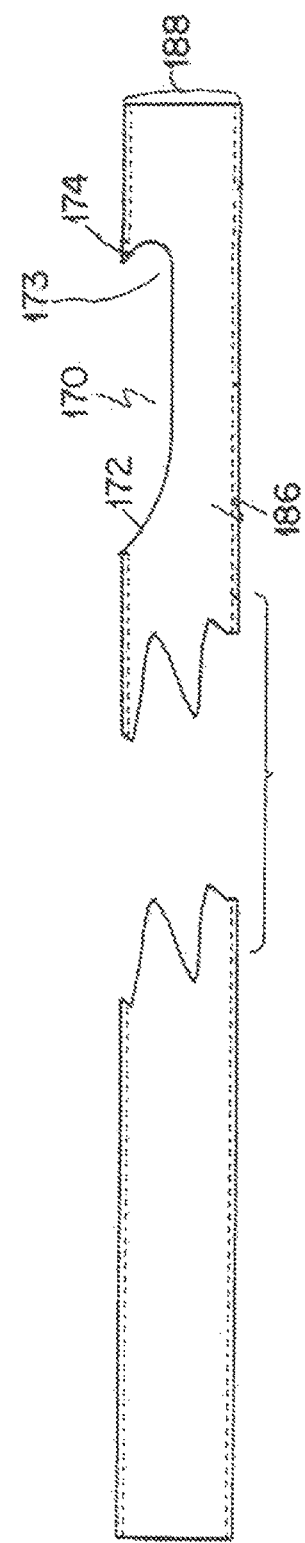

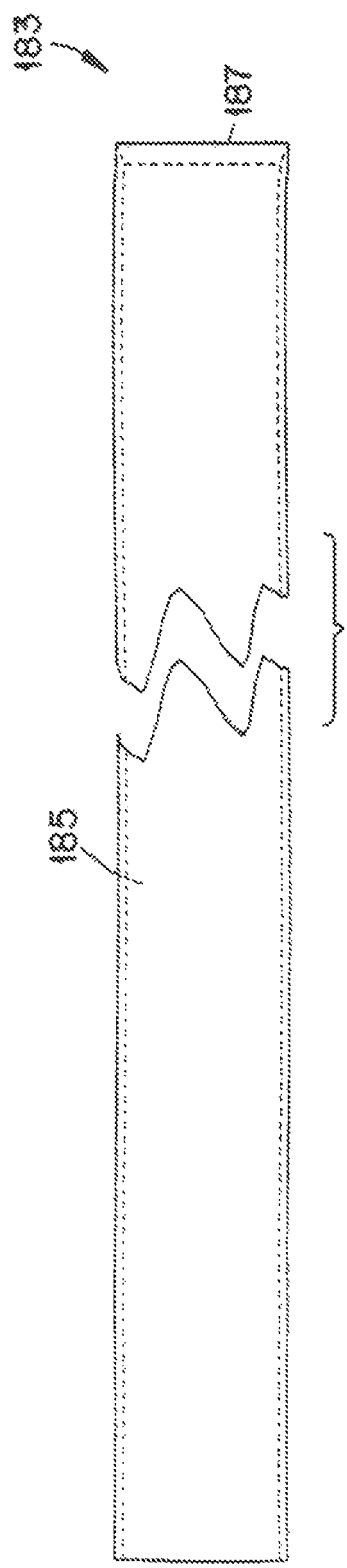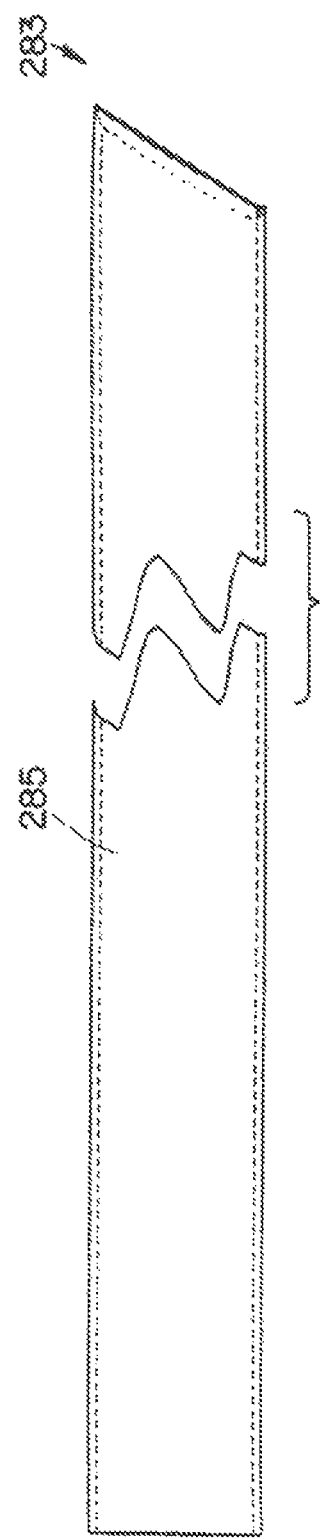

RECIPROCATING ROTARY ARTHROSCOPIC SURGICAL INSTRUMENT

CROSS REFERENCE TO RELATED APPLICATION

This application is a continuation of U.S. patent application Ser. No. 14/161,234, filed Jan. 22, 2014, now U.S. Pat. No. 9,636,130, which is a continuation of U.S. patent application Ser. No. 11/734,674, filed Apr. 12, 2007, now U.S. Pat. No. 7,922,737, which is a continuation of U.S. patent application Ser. No. 09/983,810, filed Oct. 26, 2011, now U.S. Pat. No. 7,226,459. These prior applications are incorporated herein by reference in their entireties.

TECHNICAL FIELD

This invention relates to rotary cutting surgical instruments, and more particularly, to a reciprocating rotary surgical instrument for cutting semi-rigid tissue.

BACKGROUND

Conventional arthroscopic surgical instruments generally include an outer tube and an inner member that rotates or translates axially within the outer tube. The outer tube and inner member may interact to create shear forces that cut tissue. This type of cutting is generally used to cut soft tissue, such as muscle, ligaments, and tendons.

SUMMARY

In one aspect, a surgical instrument includes a cutting member with an implement for cutting tissue, and a drive coupled to the cutting member to simultaneously rotate and translate the cutting member in response to a force applied to the drive.

One or more of the following features may be included in the surgical instrument. The drive is configured such that the cutting member reciprocates. The drive includes a drive member attached to the cutting member. The drive member includes a helical groove. The drive includes a translation piece disposed in the groove such that rotary driving of the drive member results in simultaneous reciprocation of the drive member relative to the translation piece.

In the illustrated embodiment, the drive includes an inner drive hub coupled to the drive member. The inner drive hub defines a slot and the drive member includes a key received in the slot rotary coupling the drive member to the inner drive hub such that the drive member rotates with the inner drive hub while being free to translate relative to the inner drive hub. The helical groove includes a left-hand threaded helical channel. The helical groove includes a right-hand threaded helical channel. The cutting member is attached to the drive member to move rotatably and axially with the member.

The implement is a chamfered cutting edge at a distal end of the cutting member. The chamfered edge is a straight cutting edge. Alternatively, the chamfered edge is an angled cutting edge.

The instrument includes an outer tubular member. The cutting member is received within the outer member. The outer member includes a cutting window disposed proximate to a tip of the outer member. The cutting window is an opening in the outer member exposing the cutting member to tissue. The cutting window has a U-shaped proximal end and a saddle-shaped distal end. The saddle-shaped distal end of the cutting window includes a hook.

The translation piece includes a follower received within the groove and a sealing cap over the follower. The follower is free to swivel relative to the sealing cap. The follower has an arched bridge shape. The translation piece is coupled to the drive member such that the translation piece is disposed in the helical groove and swivels to follow the helical groove as the drive member rotates.

In another aspect, a method of cutting tissue includes positioning an outer member such that tissue is located within the outer member, engaging the tissue with an inner member received within the outer member, and simultaneously rotating and translating the inner member to cut the tissue. One or more of the following features may be included. The translating is reciprocating. The outer member is oriented tangentially to the tissue.

In another aspect, a method of cutting tissue includes providing a surgical instrument having an outer member and an inner member received within the outer member for movement relative to the outer member, and applying a tangential cutting force to the tissue with the inner member to mechanically cut the tissue.

In another aspect, a method of cutting tissue includes applying a tangential cutting force to tissue with a member, and mechanically driving the member to undergo simultaneous rotation and translation. The method may include that the translation is reciprocation.

The cutting edge of conventional arthroscopic surgical instruments, such as rotary shears, have difficulty initiating a cut into semi-rigid tissue tend to bounce away from the tissue. Toothed edge geometry somewhat ameliorates this problem because the "teeth" attempt to pierce the tissue to initiate a cut. However, the efficiency of using "teeth" is limited and the limitations are more evident when cutting large volumes of semi-rigid tissue, such as meniscus or intrauterine fibroid tissue. The simultaneous rotating and reciprocating inner member of the surgical instrument of the invention overcomes these difficulties. The tangential approach to the tissue in the method of the invention limits the tendency of the instrument to bounce away from the tissue. In particular, the instrument and method provide a higher resection rate to shorten procedure length, during, e.g., fibroid and polyp resection.

The details of one or more implementations are set forth in the accompanying drawings and the description below. Other features will be apparent from the description and drawings, and from the claims.

DESCRIPTION OF DRAWINGS

FIG. 1A is a side view and 1B is a cross-sectional view taken along 1B-1B in FIG. 1A of a reciprocating rotary surgical instrument.

FIG. 2A is a top view, FIG. 2B is a cross-sectional view taken along 2B-2B in FIG. 2A, FIG. 2C is a distal end view, and FIG. 2D is a proximal end view of the inner drive hub of the reciprocating rotary surgical instrument of FIG. 1.

FIG. 3C is a cross-sectional view taken along 3C-3C in FIG. 3A, and FIG. 3D is a proximal end view of the helical member of the reciprocating rotary surgical instrument of FIG. 1.

FIG. 5B is a partial cutaway view, and FIGS. 5C and 5D are side views of the translation piece and the helical member of the surgical instrument of FIG. 1.

FIG. 6A is a side view, FIG. 6B is a cross-sectional view taken along 6B-6B in FIG. 6A, and FIG. 6C is a top view of the follower of the translation piece of the reciprocating rotary surgical instrument of FIG. 1.

FIG. 8A is a top view and FIG. 8B is a side view of the outer member of the reciprocating rotary surgical instrument of FIG. 1.

FIG. 9 is a side view of the inner member of the reciprocating rotary surgical instrument of FIG. 1.

FIG. 11 is a side view of an alternate implementation of the inner member of a reciprocating surgical instrument.

Like reference symbols in the various drawings indicate like elements.

DETAILED DESCRIPTION

Figure 3A:
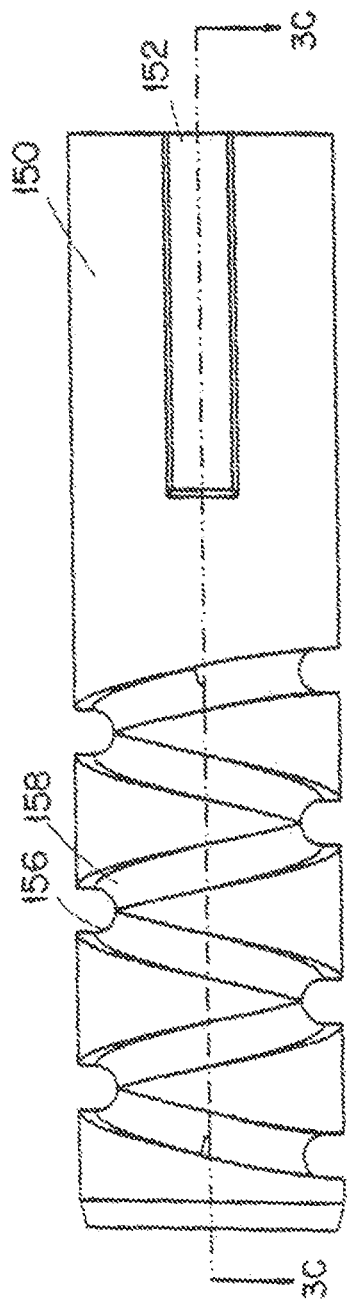
FIG. 3A is a top view.

As shown in FIGS. 1A and 1B, a cutting device 100 includes a driving end 110 and a cutting end 190. The driving end 110 is located at the proximal end of the cutting device 100. The cutting end 190 is located at the distal end of the cutting device 100.

At the driving end 110, there is an inner drive hub 130 with a drive coupler 120, and an outer hub 140. The drive coupler 120 mounts into a rotary driver (not shown), which turns the drive coupler 120 causing a helical member 150 and the inner drive hub 130 to rotate. For instance, the rotary driver is Dyonics Power Handpiece, No. 725355. The inner drive hub 130 with the drive coupler 120 is, for example, a component of Smith & Nephew disposable arthroscopic surgical instrument, No. 7205306. The helical member 150 is located within the inner drive hub 120 and the outer hub 140. The helical member 150 and a translation piece 145 are coupled together such that rotation of the helical member 150 causes linear translation of the helical member 150, as described further below.

The cutting device 100 includes an elongated inner member 185 and an elongated outer member 186, as shown in FIG. 1B. The inner member 185 is tubular with a hollow interior 184. The inner member 185 is fixed to the helical member 150 for axial and rotary motion therewith.

The outer member 186 is also tubular with a hollow interior 187. The inner member 185 is received inside the outer member 186. The outer member 186 is fixed to the outer hub 140 and does not move. The outer member 186 includes a tip 188, which is blunt, i.e., the corners are rounded. At the cutting end 190, the outer member 186 defines a cutting window 170 through a wall 186a of the outer member 186.

Referring to FIGS. 2A-2D, the inner drive hub 130 includes the drive coupler 120, a lumen 136, an aspiration opening 132, and a slot 134. The drive coupler 120 extends from the proximal end of the inner drive hub 130 and mounts in the rotary driver. Debris from the cutting end 190 of the cutting device 100 is aspirated through the aspiration opening 132. The slot 134 is disposed in a wall 131 of the inner drive hub 130. The slot 134 is like a track along one side of the inner drive hub 130. The slot 134 of the inner drive hub 130 is coupled with a key 152 of the helical member 150 (see FIG. 4B) so that rotation of the inner drive hub 130 causes the helical member 150 to rotate while allowing the helical member 150 to move axially relative to the inner drive hub 130, e.g., the key 152 axially slides along the slot 134.

Referring to FIGS. 3A-3D, the helical member 150 of the cutting device 100 is formed of a lubricious material in a tubular shape with a through lumen 159. The inner member 185 is disposed within the helical member 150 and fixed therein, for example, by epoxy, injection-molded, or over-molded plastic.

Figure 3B:
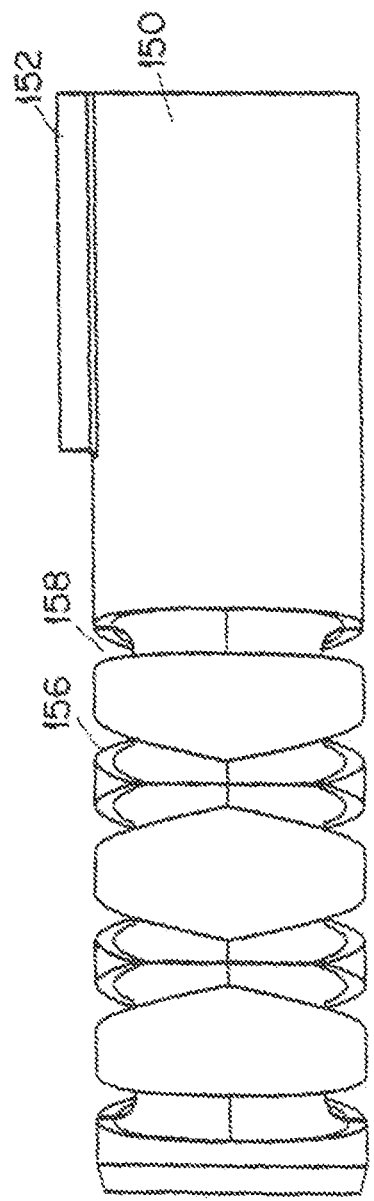
FIG. 3B is a side view.

The helical member 150 includes the key 152 and two helical channels 156, 158 disposed thereon. As shown in FIG. 3B, the key 152 is shaped like a fin and is located at the proximal end of the helical member 150. The key 152 mates with the slot 134 of the inner drive hub 130.

The two helical channels 156, 158 are disposed on a distal portion of the exterior surface of the helical member 150. One helical channel 156 is right-hand threaded; the other helical channel 158 is left-hand threaded. The pitch of the helical channels may be different or the same. The length of the distal portion of the helical member 150 with helical channels 156, 158 is longer than the length of the cutting window 170. The helical channel 156, 158 are smoothly blended together at their ends to form a continuous groove so that there is a smooth transition from one helical channel to the other helical channel at each end of the distal portion of the helical member 150.

The helical member 150 and the inner drive hub 130 are mechanically driven by the rotary driver. The helical member 150 also moves in an axial direction, e.g., reciprocates, as a result of the interaction of the translation piece 145 with the helical channels 156, 158, as described below.

Figure 4A:
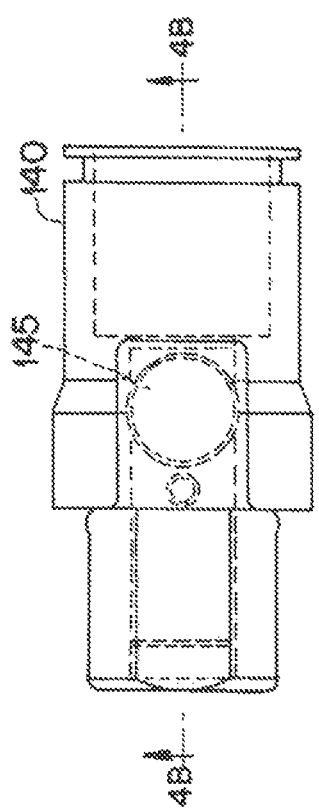
FIG. 4A is a top view.
Figure 4B:
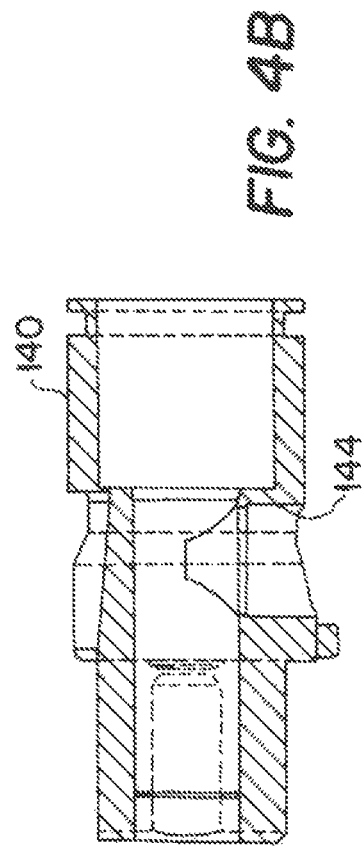
FIG. 4B is a cross-sectional view taken along 4B-4B in FIG. 4A.
Figure 4C:
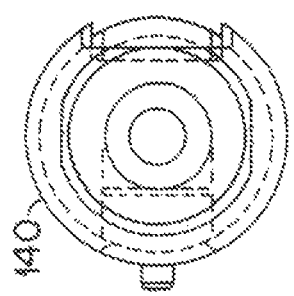
FIG. 4C is a distal end of the outer hub of the reciprocating rotary surgical instrument of FIG. 1.

Referring to FIGS. 4A-4C, the outer hub 140 of the cutting device 100 is formed of hard plastic and does not move. An example of an outer hub is a component of Smith & Nephew disposable arthroscopic surgical instrument, No. 7205306, modified with a cutout 144 for receiving the translation piece 145. The cutout 144 is disposed within a wall of the outer hub 140, for example, centrally, as in FIG. 4B, and aligned with the helical member. The translation piece 145 is located in the cutout 144 of the outer hub 140.

As shown in FIG. 1B, the outer member 186 is disposed within the outer hub 140 and fixed therein by a coupling 144 using, for example, epoxy, glue, insert molding, or spin-welding.

Figure 5A:
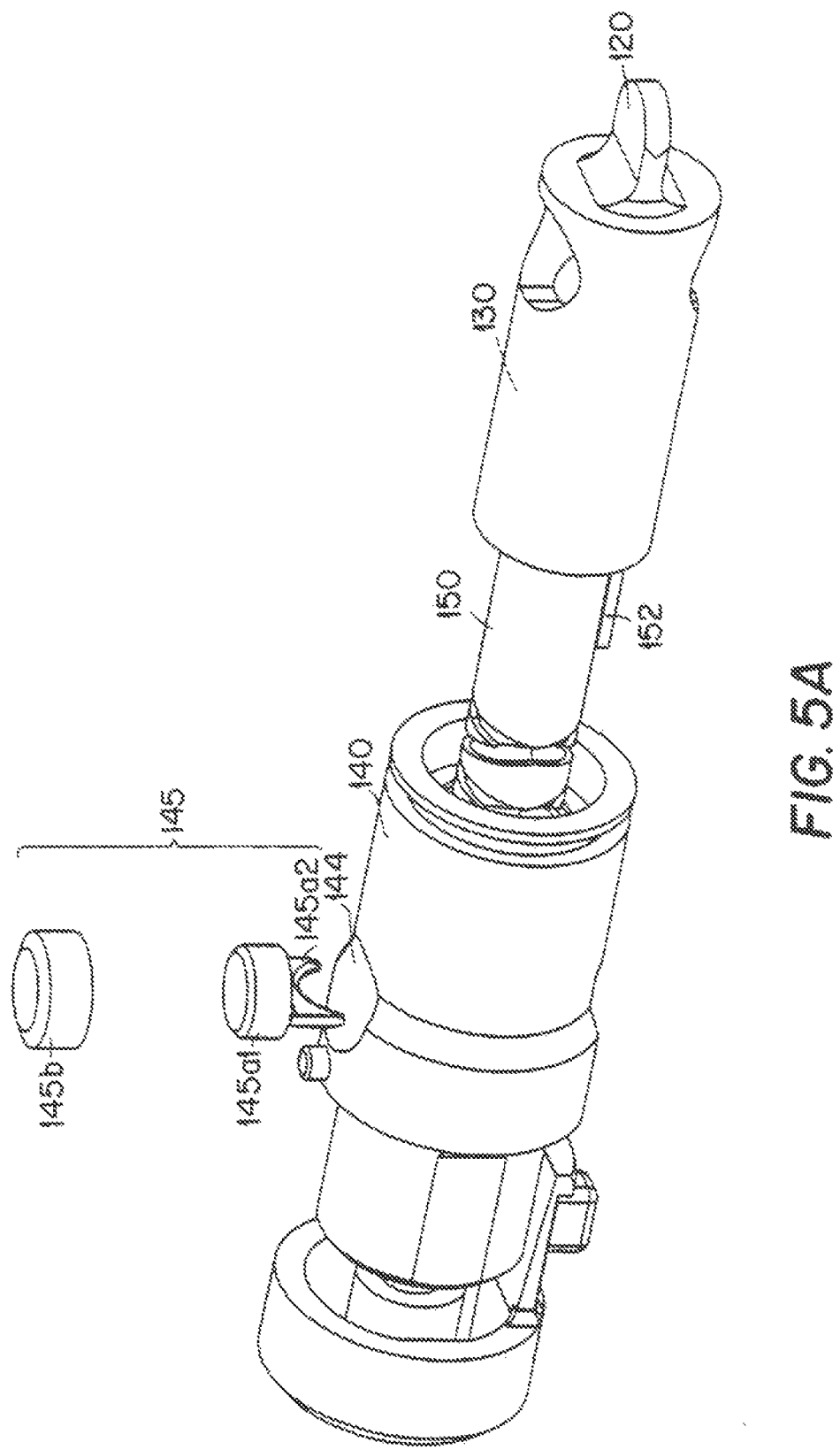
FIG. 5A is an exploded view.

Referring to FIG. 5A, the translation piece 145 includes a follower 145a and a cap 145b. Having the two helical channels 156, 158 in conjunction with the slot/key 134, 152 coupling of the inner drive hub 130 and the helical member 150, the rotary driver only needs to rotate in one direction and does not require reversal of the rotational direction upon the translation piece 145 reaching the end of one of the helical channels 156, 158.

Figure 5C:
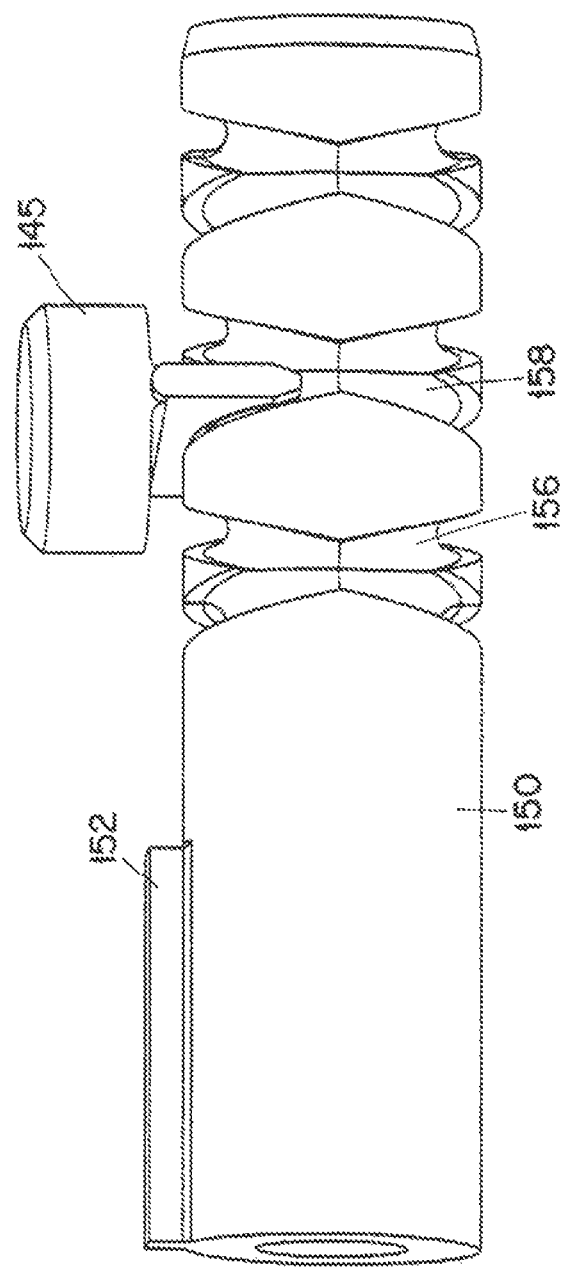

Referring to FIGS. 6A-6C, the follower 145a includes a cylindrical head 145a1 and two legs 145a2. As shown in FIGS. 5B-5D, the legs 145a2 form an arch and rest in the channels of the double helix 156, 158 formed in the distal portion of the exterior surface of the helical member 150. The arch of the legs 145a2 is dimensionally related to the diameter described by the helical channels 156, 158 of the helical member 150.

Referring particularly to FIGS. 5C and 5D, as the helical member 150 and the inner drive hub 130 are mechanically driven by the rotary driver (not shown), the follower 145a follows the helical channels 156, 158, swiveling as the follower 145a smoothly transitions from helical channel to helical channel 156, 158 at the ends of the distal portion of the helical member 150 having the helical channels 156, 158. The coupling of the follower 145a to the helical channels 156, 158 causes the helical member 150 to also translate. Thus, the inner member 185 simultaneously rotates and reciprocates to cut the tissue.

Figure 7B:
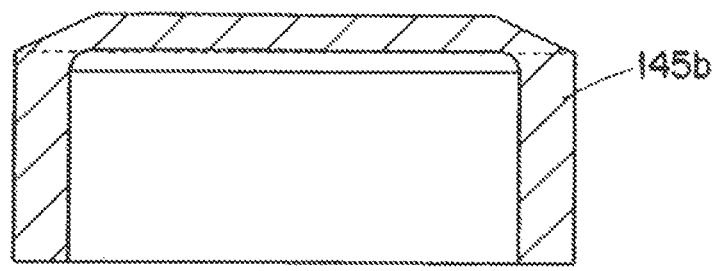
FIG. 7A is a top view and FIG. 7B is a cross-sectional view taken along 7B-7B of FIG. 7A of the cap for the follower of the translation piece of the reciprocating rotary surgical instrument of FIG. 1.
Figure 7A:
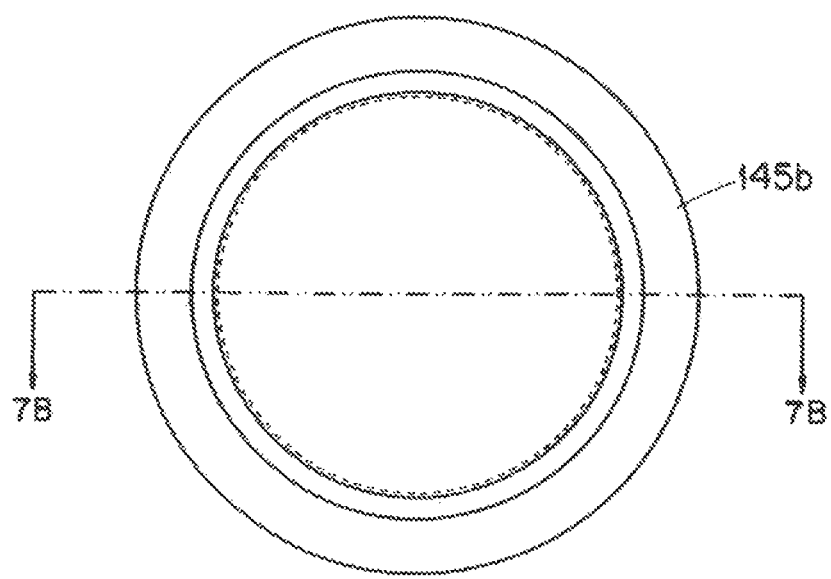

Referring to FIGS. 7A and 7B, the cap 145b of the translation piece 145 covers the follower 145a to provide a seal to allow sufficient suction to remove aspirated debris. Also, the cap 145b is a separate piece from the follower 145a in order to allow the follower 145b to swivel.

As shown in FIGS. 8A and 8B, the outer member cutting window 170 has a generally oblong shape. The proximal end 172 of the cutting window 170 is U-shaped and the distal end 173 has a saddle shape that forms a hook 174. The distal end 173 is chamfered to provide a sharp edge. The hook 174 pierces the targeted tissue to hold the tissue as the inner member 185 cuts. Also, the shape of the cutting window 170 eliminates galling between the inner and outer members 185, 186, and dulling of the cutting edge of the inner member 185.

The cutting window 170 is disposed proximate to the tip 188 of the outer member 186. The cutting window 170 exposes the inner member 185 over a length L.

Figure 10:
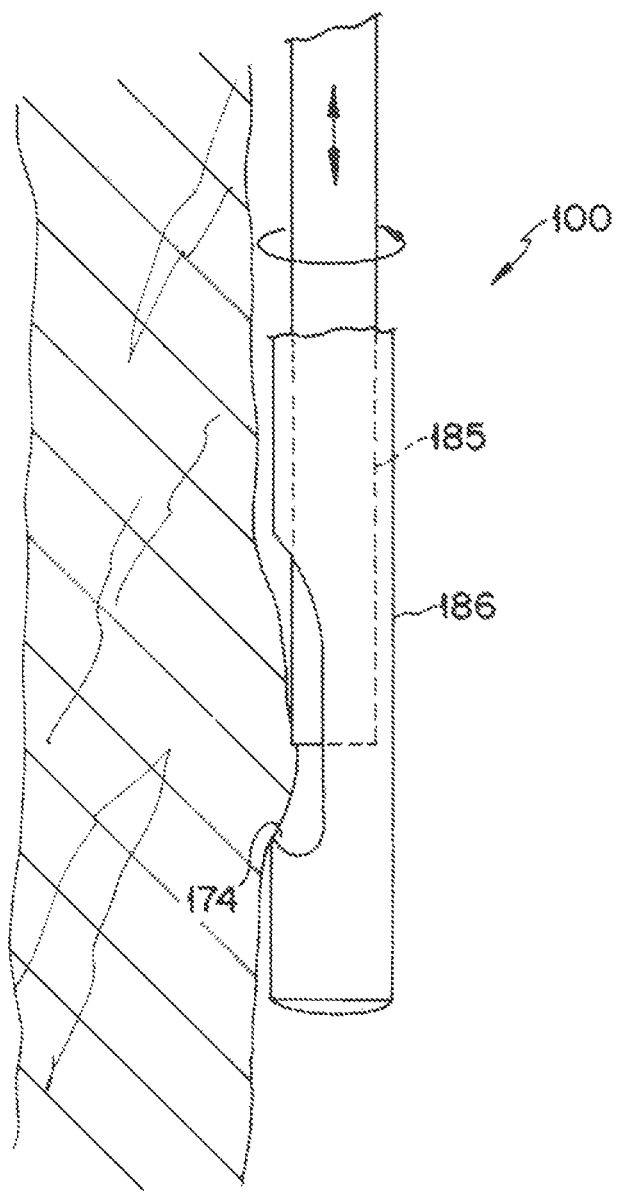
FIG. 10 illustrates a reciprocating rotary surgical instrument of FIG. 1 in use to cut tissue.

FIG. 9 shows that the inner member 185 is generally tubular with hollow interior 187. Aspiration of debris occurs through the hollow interior 187 of the inner member 185, and through the lumen of the helical member to the aspiration opening 132 of the inner drive hub 130. The distal end 183 of the inner member 185 is chamfered to a sharp edge 187 for cutting. The inner member 185 simultaneously rotates about its axis and translates along its axis to cut tissue. The cutting surface of the distal end 183 of the inner member 185 shears the tissue. For example, referring to FIG. 10, the cutting device 100 is placed tangentially against the targeted tissue such that the cutting window 170 exposes the inner member 185 to the tissue. As the inner member 185 rotates and translates, as shown by the arrows, the tissue within the cutting window catches on the hook 174 to initiate the cut and then the cutting edge 183 of the inner member 185 shears the tissue as the inner member 185 advances to cut the tissue. The cut is completed as the cutting edge 183 of the inner member 185 advances beyond the hook 174 of the cutting window 170 within the outer member 186.

FIG. 11 shows an alternative implementation of the inner member. The distal end 283 of the inner member 285 may be angled to a chamfered point so that the cut in the targeted tissue is initiated on one side and then extends across the width of the tissue. Similarly, when the cutting device is placed tangentially against the targeted tissue, the rotating and translating inner member 285 shears the tissue to be cut.

A number of implementations have been described. Nevertheless, it will be understood that various modifications may be made. For example, instead of a double helical channel, the helical member may include a single helical channel with a retractable follower and spring, or possibly, attraction and repelling forces of magnets or a solenoid could enable the rotating and reciprocating movements. Also, alternatively, the inner and outer members may have a cross-sectional shape other than circular. Additionally, the shape of the hook of the outer member may be modified in order to improve grasping of the tissue or grasping a larger volume of tissue. Accordingly, other implementations are within the scope of the following claims.

What is claimed is:

1. A driving assembly of a surgical instrument, comprising:
    a drive coupler configured to receive a rotational input;
    a helical member operably coupled to the drive coupler such that rotation of the drive coupler rotates the helical member, the helical member defining a helical groove having a first threaded helical channel and a second threaded helical channel, the first and second threaded helical channels blended together at their ends to form a continuous groove such that there is a smooth transition from the first threaded helical channel to the second threaded helical channel; and
    a translation piece engaged within the helical groove such that the helical member provides both a rotational output and translational output in response to the rotational input, wherein the helical member is adapted to connect to a cutting member to provide the rotational output and the translational output thereto.

2. The driving assembly according to claim 1, wherein the drive coupler is adapted to connect to a rotary driver configured to provide the rotational input to the drive coupler.

3. The driving assembly according to claim 1, wherein the first threaded helical channel defines a right-handed configuration, and wherein the second threaded helical channel defines a left-handed configuration.

4. The driving assembly according to claim 1, further comprising an outer hub at least partially housing the helical member and the translation piece therein.

5. The driving assembly according to claim 4, wherein the drive coupler extends proximally from the outer hub.

6. The driving assembly according to claim 4, wherein the translation piece extends through a cut-out defined within the outer hub and is longitudinally fixed within the cut-out.

7. The driving assembly according to claim 1, wherein the helical member is operably coupled to the drive coupler via a key-slot arrangement rotationally coupling the drive coupler to the helical member and permitting translation of the helical member relative to the drive coupler.

8. The driving assembly according to claim 1, wherein helical groove extends at least two full revolutions about the drive member.

9. The driving assembly according to claim 1, wherein the translation piece is configured to swivel when moving between the first threaded the helical channel and the second threaded helical channel.

10. A driving assembly of a surgical instrument, comprising:
    a drive coupler configured to receive a rotational input;
    a helical member operably coupled to the drive coupler such that rotation of the drive coupler rotates the helical member, the helical member defining a helical groove having a first threaded helical channel and a second threaded helical channel, the first and second threaded helical channels coupled together at their ends to define transitions therebetween, wherein the first threaded helical channel defines a first pitch and wherein the second threaded helical channel defines a second pitch different from the first pitch; and
    a translation piece engaged within the helical groove such that the helical member provides both a rotational output and translational output in response to the rotational input, wherein, as a result of the different first and second pitches, the translation output defines a first speed in a first direction and a second, different speed in a second, opposite direction.

11. The driving assembly according to claim 10, wherein the drive coupler is adapted to connect to a rotary driver configured to provide the rotational input to the drive coupler.

12. The driving assembly according to claim 10, wherein the helical member is adapted to connect to a cutting member to provide the rotational output and the translational output thereto, and wherein the cutting member is configured to translate the first speed in the first direction and the second speed in the second, opposite direction.

13. The driving assembly according to claim 10, wherein the first threaded helical channel defines a right-handed configuration, and wherein the second threaded helical channel defines a left-handed configuration.

14. The driving assembly according to claim 10, further comprising an outer hub at least partially housing the helical member and the translation piece therein.

15. The driving assembly according to claim 14, wherein the drive coupler extends proximally from the outer hub.

16. The driving assembly according to claim 14, wherein the translation piece extends through a cut-out defined within the outer hub and is longitudinally fixed within the cut-out.

17. The driving assembly according to claim 10, wherein the helical member is operably coupled to the drive coupler via a key-slot arrangement rotationally coupling the drive coupler to the helical member and permitting translation of the helical member relative to the drive coupler.

18. The driving assembly according to claim 10, wherein helical groove extends at least two full revolutions about the drive member.

19. The driving assembly according to claim 10, wherein the translation piece is configured to swivel when moving between the first threaded helical channel and the second threaded helical channel.

\* \* \* \* \*